(12) United States Patent
Massie

(10) Patent No.: US 8,498,374 B2
(45) Date of Patent: *Jul. 30, 2013

(54) DENTAL AND ORTHOPEDIC DENSITOMETRY MODELING SYSTEM AND METHOD

(75) Inventor: Ronald E. Massie, Lake Ozark, MO (US)

(73) Assignee: Osseo Imaging, LLC, Topeka, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/619,356

(22) Filed: Sep. 14, 2012

(65) Prior Publication Data

US 2013/0022164 A1     Jan. 24, 2013

Related U.S. Application Data

(63) Continuation of application No. 13/367,150, filed on Feb. 6, 2012, and a continuation of application No. 12/250,423, filed on Oct. 13, 2008, now Pat. No. 8,126,112, which is a continuation-in-part of application No. 11/932,809, filed on Oct. 31, 2007, now Pat. No. 8,073,101, which is a continuation-in-part of application No. 11/224,472, filed on Sep. 12, 2005, now Pat. No. 7,839,970, which is a continuation of application No. 10/351,567, filed on Jan. 24, 2003, now Pat. No. 6,944,262, which is a continuation-in-part of application No. 10/134,153, filed on Apr. 27, 2002, now abandoned, which is a continuation of application No. 09/452,348, filed on Dec. 1, 1999, now Pat. No. 6,381,301.

(51) Int. Cl.
*A61B 6/03* (2006.01)
*A61B 6/14* (2006.01)
*H05G 1/60* (2006.01)

(52) U.S. Cl.
USPC .................................. 378/5; 378/19

(58) Field of Classification Search
USPC .................... 378/5, 16, 15, 21, 19, 38, 39, 62
See application file for complete search history.

(56) References Cited

U.S. PATENT DOCUMENTS 3,949,229 A    4/1976  Albert
4,104,532 A    8/1978  Weiss
(Continued)

FOREIGN PATENT DOCUMENTS

CA    2390334    11/2008
EP    0180482    5/1986
(Continued)

OTHER PUBLICATIONS

"Final Decision for Rejection", Japan Patent Application No. 2006-502953 based on PCT/US2001/001825, (Mar. 30, 2010).

(Continued)

*Primary Examiner* — Irakli Kiknadze
(74) *Attorney, Agent, or Firm* — Law Office of Mark Brown, LLC; Mark E. Brown; Christopher M. DeBacker

(57) ABSTRACT

A dental and orthopedic densitometry modeling system includes a controller with a microprocessor and a memory device connected to the microprocessor. An input device is also connected to the microprocessor for inputting diagnostic procedure parameters and patient information. X-ray equipment including an X-ray source and an X-ray detector array are connected to a positioning motor for movement relative to a patient's dental or orthopedic structure in response to signals from the microprocessor. The output consists of a tomographical densitometry model. A dental/orthopedic densitometry modeling method involves moving the X-ray equipment across a predetermined scan path, emitting dual-energy X-ray beams, and outputting an image color-coded to correspond to a patient's dental or orthopedic density.

24 Claims, 2 Drawing Sheets

U.S. PATENT DOCUMENTS

| | | |
|---|---|---|
| 4,188,537 A | 2/1980 | Franke |
| 4,239,971 A | 12/1980 | Cushman |
| 4,259,583 A | 3/1981 | Albert |
| 4,628,356 A | 12/1986 | Spillman |
| 4,741,007 A | 4/1988 | Virta et al. |
| 4,783,793 A | 11/1988 | Virta et al. |
| 4,813,060 A | 3/1989 | Heubeck et al. |
| 4,823,369 A | 4/1989 | Guenther et al. |
| 4,856,038 A | 8/1989 | Guenther et al. |
| 4,941,164 A | 7/1990 | Schuller et al. |
| 4,985,907 A | 1/1991 | Moteni |
| 5,093,852 A | 3/1992 | Nishikawa et al. |
| 5,195,114 A | 3/1993 | Sairenji et al. |
| 5,214,686 A | 5/1993 | Webber |
| 5,224,140 A | 6/1993 | Virta et al. |
| 5,267,293 A | 11/1993 | Virta |
| 5,306,306 A | 4/1994 | Bisek et al. |
| 5,335,260 A | 8/1994 | Arnold |
| 5,480,439 A | 1/1996 | Bisek et al. |
| 5,503,559 A | 4/1996 | Vari |
| 5,528,645 A | 6/1996 | Koivisto |
| 5,533,080 A | 7/1996 | Pelc |
| 5,579,361 A | 11/1996 | Augais et al. |
| RE35,423 E | 1/1997 | Adams et al. |
| 5,677,940 A | 10/1997 | Suzuki et al. |
| 5,784,429 A | 7/1998 | Arai |
| 5,785,041 A | 7/1998 | Weinstein et al. |
| 5,793,837 A | 8/1998 | Mezhinsky et al. |
| 5,828,720 A | 10/1998 | Syrjanen |
| 5,828,721 A | 10/1998 | Schulze-Ganzlin et al. |
| 5,828,722 A | 10/1998 | Ploetz et al. |
| 5,835,555 A | 11/1998 | Barry et al. |
| 5,836,876 A | 11/1998 | Dimarogonas |
| 5,838,765 A | 11/1998 | Gershman |
| RE36,162 E | 3/1999 | Bisek et al. |
| 5,900,883 A | 5/1999 | Crucs |
| 5,917,882 A | 6/1999 | Khutoryansky et al. |
| 5,917,883 A | 6/1999 | Khutoryansky et al. |
| 5,930,327 A | 7/1999 | Lin |
| 5,995,583 A | 11/1999 | Schick et al. |
| 6,038,287 A | 3/2000 | Miles |
| 6,069,935 A | 5/2000 | Schick et al. |
| 6,233,305 B1 | 5/2001 | Muller |
| 6,320,931 B1 | 11/2001 | Arnold |
| 6,332,891 B1 | 12/2001 | Himes |
| 6,381,301 B1 | 4/2002 | Massie |
| 6,385,283 B1 | 5/2002 | Stein et al. |
| 6,398,549 B1 | 6/2002 | Koivisto et al. |
| 6,405,071 B1 | 6/2002 | Analoui |
| 6,424,694 B1 | 7/2002 | Molteni |
| 6,452,997 B1 | 9/2002 | Muller et al. |
| 6,466,641 B1 | 10/2002 | Virta et al. |
| 6,470,069 B1 | 10/2002 | Muller |
| 6,496,558 B2 | 12/2002 | Graumann |
| 6,516,216 B1 | 2/2003 | Fontenot et al. |
| 6,530,688 B1 | 3/2003 | Müller |
| 6,664,986 B1 | 12/2003 | Kopelman et al. |
| 6,690,761 B2 | 2/2004 | Lang et al. |
| 6,821,116 B2 | 11/2004 | Severance |
| 7,099,428 B2 | 8/2006 | Clinthorne et al. |
| 7,203,273 B2 | 4/2007 | Linnosaari |
| 2002/0114425 A1 | 8/2002 | Lang et al. |
| 2002/0178032 A1 | 11/2002 | Benn et al. |

FOREIGN PATENT DOCUMENTS

| | | |
|---|---|---|
| EP | 0314506 | 5/1989 |
| EP | 0652433 | 5/1995 |
| EP | 1237483 | 11/2008 |
| WO | WO-9311707 | 6/1993 |
| WO | WO-0138824 | 5/2001 |
| WO | WO-01/39667 | 6/2001 |

OTHER PUBLICATIONS

"International Search Report", PCT/US00/32905, (Jan. 26, 2001).
"Notice of Reason for Rejection", Japan Appl. No. 2001-541403 based on PCT/US00/32905, (Mar. 19, 2010).
"Notice of Reason for Rejection", Japan Patent Application No. 2006-502953 based on PCT/US2004/001825, (Aug. 3, 2009).
"Notice of Reason for Rejection", Japan Patent Application No. 2001-541403 based on PCT/US00/32905, (Nov. 24, 2009).
"Supplemental European Search Report", Massie Application No. 04704878.0, PCT/US2004001825, Jun. 10, 2008.
"Written Opinion of the ISA", PCT/US/04/01825, Feb. 25, 2005.
Boyde, A. et al., "The Mineralization Density of Iliac Crest Bone From Children with Osteogenesis Imperfecta", A. Boyde, R. Travers, F.H. Glorieux, S. J. Jones, *The Mineralization Density of Iliac Crest Bone From Children with Osteogenesis Imperfecta, Calcified Tissue International*, vol. 64 Issue 3, Mar 1999, pp. 185-190, (Mar. 1999), 185-90.
Branemark, M.D., Ph.D., Ingvar et al., "Tissue-Integrated Prosthese, Osseointegration in clinical denistry", *Quintessence Publishing Co., Inc., 1985*, 11-70.
Elsasser, URS, P., et al., "Bone Density Measurement with Computed Tomography", *British Medical Bulletin* vol. 36, No. 3, (1980), 293-296.
Exner, G., M., et al., "Bone Densitometry Using Computed Tomography", *British Journal of Radiology*, vol. 52, (1979), 14-23.
Krennmair, Gerald, MD et al., "Maxillary Sinus Aspergillosis: Diagnosis and Differentiation of the Pathogenesis Based on Computed Tomography Densitometry of Sinus Concretions", American Association of Oral and Maxillofacial Surgeons, (1995), 657-663.
"Apteryx, Inc. 501(k) Summary for Xray Vision—K983111", http://www.accessdata.fda.gov/cdrh_docs/pdf/K983111.pdf, (Nov. 16, 1998).
"Sirona Dental Systems GmbH Special 501(k) Summary for SIDEXIS Digital Radiography Imaging System—K992644", http://www.accessdata.fda.gov/cdrh_docs/pdf/K992644.pdf, (Aug. 23, 1999).
Lindh, et al., "Quantitative Computed Tomography of Trabecular Bone in the Mandible", *Dentomaxillofac. Radiol., vol. 25, No. 3, pp. 146-150*, (Jun. 1996).

DENTAL AND ORTHOPEDIC DENSITOMETRY MODELING SYSTEM AND METHOD

CROSS-REFERENCE TO RELATED APPLICATIONS

This application is a continuation of and claims priority in Ser. No. 13/367,150, filed Feb. 6, 2012, which is a continuation of and claims priority in Ser. No. 12/250,423, filed Oct. 13, 2008, now U.S. Pat. No. 8,126,112, which is a continuation-in-part of Ser. No. 11/932,809, filed Oct. 31, 2007, now U.S. Pat. No. 8,073,101, which is a continuation-in-part of Ser. No. 11/224,472, filed Sep. 12, 2005, now U.S. Pat. No. 7,839,970, which is a continuation of Ser. No. 10/351,567, filed Jan. 24, 2003, now U.S. Pat. No. 6,944,262, which is a continuation-in-part of Ser. No. 10/134,153, filed Apr. 27, 2002, now abandoned, which is a continuation of Ser. No. 09/452,348, filed Dec. 1, 1999, now U.S. Pat. No. 6,381,301, which are all incorporated herein by reference.

BACKGROUND OF THE INVENTION

1. Field of the Invention

The present invention relates generally to dental and orthopedic diagnosis and treatment, and in particular to a densitometry modeling system and method.

2. Description of the Related Art

The field of dental diagnostics is generally concerned with locating pathologies in the dental structure, i.e., the teeth and the surrounding tissue and bone. Three of the most common pathologies are: 1) caries associated with decay; 2) fractures; and 3) apical abscesses. The system and method of the present invention are primarily, but not exclusively, concerned with detecting these pathologies and with orthopedics.

Early detection of dental pathologies is very important in minimizing damage. Conventional diagnosis procedures are generally performed using dental X-rays (both fixed beam and scanning beam), explorers, and other conventional equipment.

Incipient caries, particularly those located beneath the enamel surface, often go undetected with conventional equipment. When such caries are finally found, considerable damage to tooth structure may have already occurred. Subsurface, incipient caries are located almost entirely within the enamel layer of the teeth. They are sometimes referred to as "smooth surface" caries and are particularly difficult to locate using conventional diagnostic equipment and procedures. By the time such incipient caries are located, the extent of the damage is often 17% to 23% greater than it would appear to be on a conventional X-ray negative.

Dental fractures can result from bruxism (teeth grinding), trauma, etc. Dental structure which is weakened by various causes, such as decalcification, is particularly susceptible to fractures. Fractures can assume various configurations, including craize line patterns. Fracture patterns and configurations can be particularly difficult to locate using conventional X-ray equipment and procedures. For example, fractures which are generally parallel to the X-ray beam are often undetectable on an X-ray negative. Undetected, and hence untreated, fractures can provide direct paths through the enamel layer of the teeth whereby bacteria can invade the dentin and pulp layers. Pathologies in the dentin and pulp layers are often associated with considerable pain and tooth loss.

Apical abscesses comprise yet another dental condition which can be difficult to diagnose with conventional equipment, particularly in the early stages. Advanced apical abscesses can cause considerable pain because they involve the neurovascular bundles located in the root canals. Early detection of apical abscesses can lead to appropriate, early-stage treatment, thus avoiding advanced disease processes with resultant pain, swelling, and/or space involvement which left untreated could ultimately result in death.

Tomography or sectional radiography techniques using scanning X-ray beams have previously been employed for dental applications. For example, U.S. Pat. No. 4,188,537; U.S. Pat. No. 4,259,583; U.S. Pat. No. 4,823,369; U.S. Pat. No. 4,856,038; and U.S. Pat. No. 5,214,686 all relate to dental X-ray diagnosis utilizing scanning techniques and are incorporated herein by reference.

In the medical field, densitometry procedures are used for measuring bone morphology density (BMD) by utilizing scanning X-ray beam techniques. Examples are shown in U.S. Pat. No. 5,533,080; U.S. Pat. No. 5,838,765; and Re. 36,162, which are incorporated herein by reference. Medical applications of densitometry include the diagnosis and treatment of such bone diseases as osteoporosis.

The availability of relatively fast computers with large memories at reasonable costs has led to the digitalization of X-ray images for mapping BMD models in various formats. For example, BMD images use color to identify varying densities. Digital BMD patient models are also used for comparison purposes with standard models and with patients' own prior BMD histories. Age correction factors can be applied to patients' models for diagnosing and monitoring the onset and progress of such medical conditions as osteoporosis and the like. The present invention utilizes such densitometry modeling and mapping techniques for dental applications.

In addition to pathology detection and diagnosis, the present invention has applications in monitoring osseointegration. Osseointegration occurs at the interface between bone structures and prostheses, such as implants and replacement joints. For example, dental implants osseointegrate with patients' dental structure. The application of tomographical densitometry techniques to osseointegration monitoring can provide the dental or medical practitioner with important information in evaluating the effectiveness of implant procedures.

Heretofore there has not been available a system or method for applying the technology of densitometry to dental and medical applications such as the detection of caries and decalcification and the monitoring of osseointegration in connection with dental and medical prostheses.

SUMMARY OF THE INVENTION

In the practice of the present invention, a dental and orthopedic densitometry modeling system utilizes a controller with a microprocessor and memory. An input device inputs data to the microprocessor for controlling the operation of the modeling system and for providing a database including densitometry parameters for comparison with a patient's densitometry model. The controller controls the operation of X-ray equipment, which is adapted for scanning patients' dental and orthopedic structures along preprogrammed scan paths. The X-ray output is processed by the microprocessor for creating a densitometry model, which can be output in various formats. In the practice of the method of the present invention, a patient and the X-ray equipment are positioned relative to each other. A controller is preprogrammed with a scan path and with data corresponding to the patient. The X-ray equipment emits and detects X-ray beams at first and second energy levels to provide densitometry output. The densitometry output is digitized and merged to provide a tomographic model, which can be compared to predetermined parameters unique to the patient. The model can be output in various formats, including a visual image color-coded to depict varying dental and orthopedic structure densities.

PRINCIPLE OBJECTS AND ADVANTAGES OF THE INVENTION

The principle objects and advantages of the present invention include: providing a dental and orthopedic diagnostic application for densitometry; providing such an application which includes a method for modeling dental and orthopedic structure using densitometry; providing such a method which includes dual-energy, X-ray emission and detection; providing such a method which includes providing a color-coded output model showing dental density; providing such a method which detects incipient caries; providing such a method which is adapted for detecting decalcification beneath the surface of the dental enamel layer; providing such a method which employs scanning X-ray techniques; providing such a method which utilizes commercially available tomography equipment; providing such a method which detects dental fractures; providing such a method which detects dental apical abscesses; providing such a method which detects dental pathologies at the micron level; providing such a method which facilitates the monitoring of decalcification in dental structures for determining appropriate treatment; providing such a method which is adaptable for monitoring osseointegration; providing such a method which can be practiced with relatively minor changes to existing densitometry equipment; and providing such a method which is economical in operation and particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE PREFERRED EMBODIMENTS

I. Introduction and Environment

Figure 1:
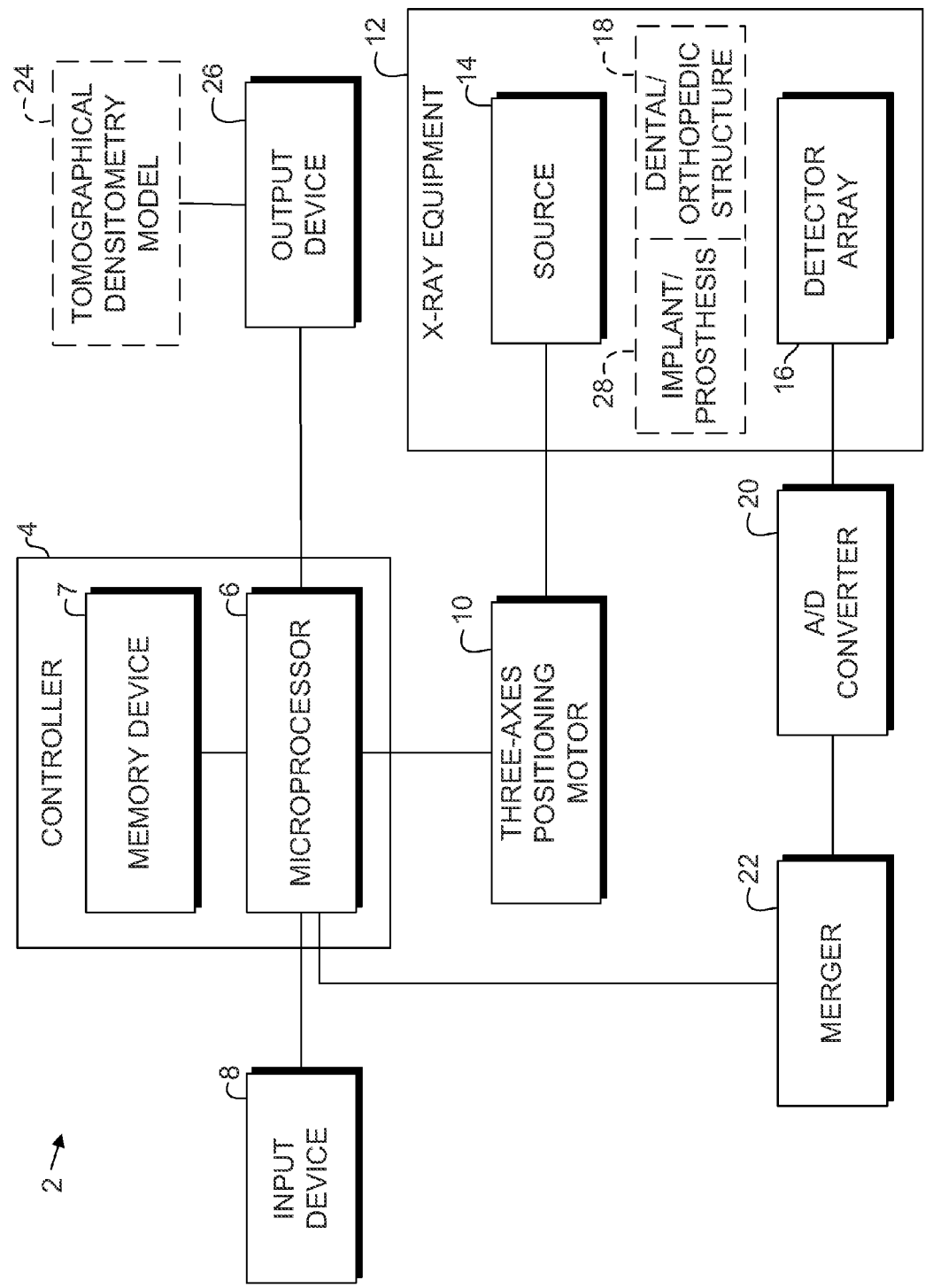
FIG. 1 is a schematic, block diagram of a dental and orthopedic densitometry modeling system embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

II. Dental Densitometry Modeling System 2

Referring to the drawings in more detail, the reference numeral 2 generally designates a dental and orthopedic densitometry modeling system embodying the present invention. The system 2 includes a controller 4 with a microprocessor 6 connected to a digital memory device 7. The hardware components of the controller 4, i.e., the microprocessor 6 and the memory device 7, can comprise any of a number of suitable hardware devices which are commercially available and are suitable for this application. In addition to various programmable logic devices (PLDs) and special-purpose microprocessors, general purpose, commercially available personal computers can be utilized in the controller 4. The controller 4 can be programmed in any suitable manner utilizing any of a variety of commercially available programming languages and software development systems.

The microprocessor 6 is adapted to receive input from one or more input devices 8, such as a keyboard, a pointing device (e.g., a mouse), a communications link, or another computer. Without limitation on the generality of useful data which can be input via the input device(s) 8, such data can include: 1) a patient's dental and orthopedic records, including previous tomographical densitometry models; 2) baseline tomographical densitometry models, which can be adjusted to accommodate for such factors as age, gender, size, weight, etc.; and 3) a preprogrammed scan path for the X-ray equipment.

The microprocessor 6 controls a positioning motor 10 which is operably connected to X-ray equipment 12 and is adapted for moving same through three axes of movement. Examples of X-ray equipment adaptable for use with the present invention are disclosed in U.S. Pat. No. 5,533,080; No. 5,838,765; and No. Re. 36,162, which are incorporated herein by reference. The X-ray equipment 12 includes an X-ray beam source 14 and a detector array 16. The X-ray beam can be suitably collimated to assume any suitable configuration, such as fan, pencil, cone, etc. With the scanning technique disclosed, a restricted (i.e., collimated) beam is preferred. The source and the detector array 14, 16 are adapted for positioning on either side of a patient's dental/orthopedic structure 18.

Analog signals from the detector array 16 are output to an analog-to-digital (A/D) convertor 20, from which digitized signals are transmitted to a merger device 22 for merging into formats suitable for processing and analyzing by the microprocessor 6. The microprocessor 6, using data from the merger device 22, creates a tomographical densitometry model 24 which is transmitted to an output device or devices 26. Without limitation on the generality of useful output devices 26, it can comprise a monitor, a display, a printer, a communications link, and/or another computer. For example, a color printer can be utilized to provide a color-coded graphical representation of the tomographical densitometry model 24. The color coding can correspond to densities, thus identifying potential problem areas where decalcification has occurred and resulted in lower density. The tomographical densitometry model 24 can also be useful for monitoring osseointegration, since the density of the dental/orthopedic structure 18 (tissue and bone) in the vicinity of an implant 28 or other prostheses can provide an important diagnostic tool for the use of the dental or medical practitioner in assessing the effectiveness of an implant or prosthetic procedure. The tomographical densitometry model 24 is also entered into the computer's memory device 7.

III. Dental and Orthopedic Densitometry Modeling Method

Figure 2:
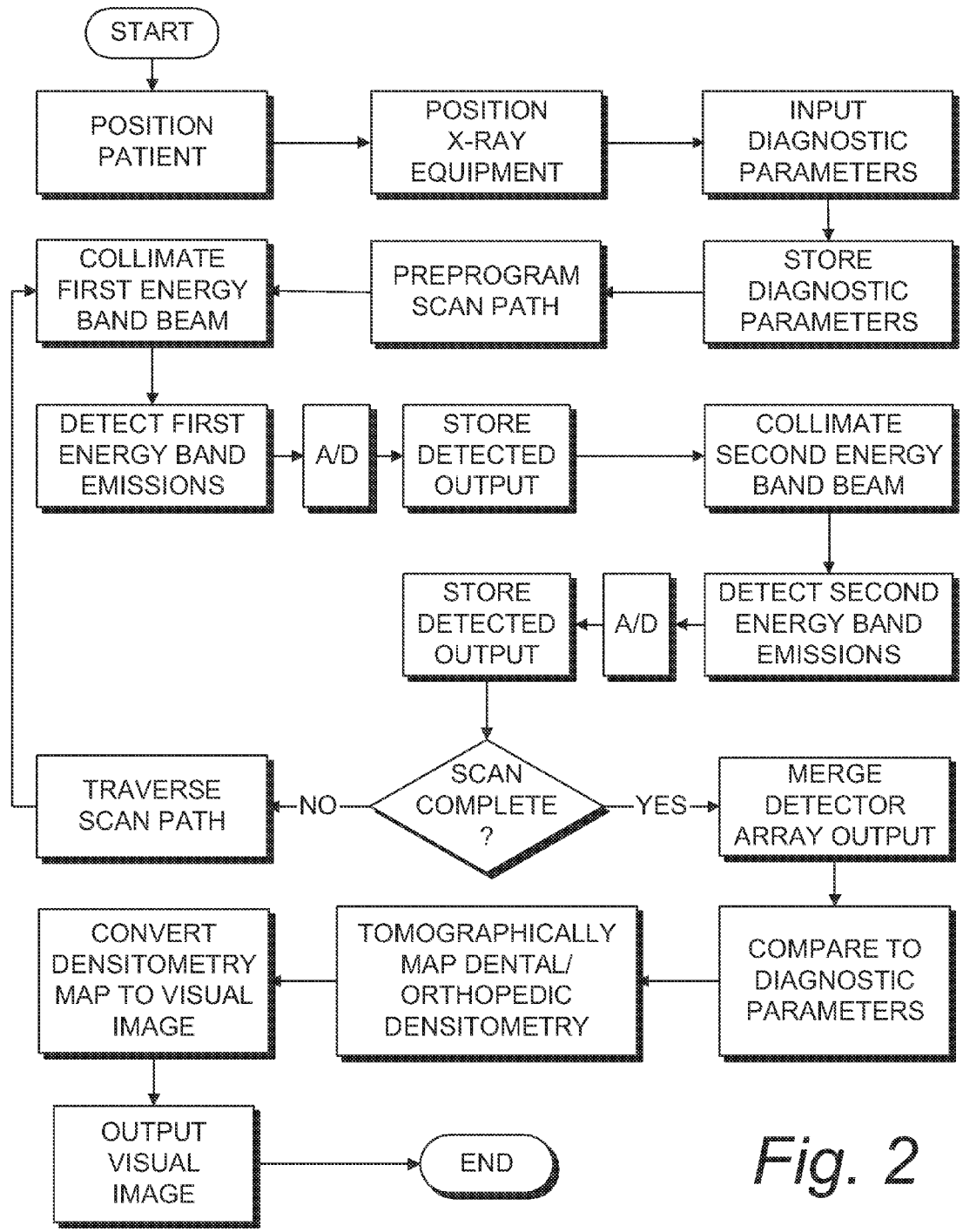
FIG. 2 is a flowchart of a dental and orthopedic densitometry modeling method embodying the present invention.

FIG. 2 is a flowchart of a dental and orthopedic densitometry method embodying the present invention. The method steps include positioning a patient and positioning the X-ray equipment relative to the patient, i.e., with the patient's dental/orthopedic structure to be examined located between the X-ray source 14 and the detector array 16.

Diagnostic parameters are input to the system and can comprise, for example, the patient's prior tomographical densitometry models and standardized models. The tomographical densitometry models can be corrected and/or adjusted to account for a patient's age, gender, physical characteristics, etc. The input diagnostic parameters can be stored in the computer's memory device. A scan path for the X-ray equipment is preprogrammed in the computer.

The scanning procedure is commenced by collimating a first energy band beam, detecting emissions from same with a detector array, and converting the analog output of the detector array to a digital signal. The digital signal is output for storage in the computer. The steps of collimating the energy band beam and detecting, digitizing and storing same are repeated for a second energy band beam. The Bisek et al. U.S. Pat. No. Re. 36,162 discloses the use of dual-energy X-ray beams in medical densitometry applications. As discussed therein, dual-energy densitometry can result in a more accurate patient model.

The X-ray equipment then traverses the preprogrammed scan path and the first/second energy band steps are repeated until the scanning procedure is complete. The digitized detector array output is merged and compared to the diagnostic parameters which are stored in the computer's memory. The dental/orthopedic densitometry is tomographically modeled and output, for example to a monitor or printer for converting the model to a visual image. The visual image is output in a visible form for use by dental and medical practitioners.

What is claimed as new and desired to be secured by Letters Patent is:

1. A system for tomographically modeling a dental structure, the system comprising:
   a controller with a microprocessor and a memory device connected to the microprocessor, said controller being adapted for storing computed tomographic models of a dental structure;
   an input device connected to the microprocessor;
   a positioning motor connected to the microprocessor and responsive to commands from said microprocessor;
   X-ray equipment including an X-ray source, a detector array, and a restricted beam device;
   a convertor for converting a signal from said detector array, said convertor being connected to said detector array and to said microprocessor; and
   an output device connected to said microprocessor and adapted for receiving a tomographic model from said microprocessor.

2. The system according to claim 1, wherein said restricted beam device comprises a dual-energy level restricted beam device.

3. The system according to claim 1, wherein said tomographic model received by said output device is a 3D tomographic model.

4. The system according to claim 1 wherein:
   said x-ray source travels along a single axis; and
   said x-ray source simultaneously rotates around said single axis.

5. The system according to claim 1, wherein:
   said controller is adapted for storing a first tomographic model and a second tomographic model;
   said first tomographic model is a preexisting, commercially available standard model;
   said second tomographic model is a current patient model; and
   said controller is further adapted to compare said first tomographic model with said second tomographic model.

6. The system according to claim 1, wherein:
   said controller is adapted for storing a first tomographic model and a second tomographic model;
   said first tomographic model is a preexisting patient model;
   said second tomographic model is a current patient model; and
   said controller is further adapted to compare said first tomographic model with said second tomographic model.

7. The system according to claim 1, wherein said X-ray source emits an X-ray beam comprising a cone configuration.

8. The system according to claim 7, wherein said restricted beam device comprises a dual-energy level restricted beam device.

9. The system according to claim 7, wherein said tomographic model received by said output device is a 3D tomographic model.

10. The system according to claim 7 wherein:
    said x-ray source travels along a single axis; and
    said x-ray source simultaneously rotates around said single axis.

11. The system according to claim 7, wherein:
    said controller is adapted for storing a first tomographic model and a second tomographic model;
    said first tomographic model is a preexisting, commercially available standard model;
    said second tomographic model is a current patient model; and
    said controller is further adapted to compare said first tomographic model with said second tomographic model.

12. The system according to claim 7, wherein:
    said controller is adapted for storing a first tomographic model and a second tomographic model;
    said first tomographic model is a preexisting patient model;
    said second tomographic model is a current patient model; and
    said controller is further adapted to compare said first tomographic model with said second tomographic model.

13. A tomographic modeling system comprising:
    a controller with a microprocessor and a memory device connected to the microprocessor, said controller being adapted for creating, storing, and comparing 3D digital tomographic models of an object without the use of fiducial markers of said object;
    an input device connected to the microprocessor;
    a positioning motor connected to the microprocessor and responsive to commands from said microprocessor;
    X-ray equipment including an X-ray source, a detector array, and a restricted beam device;
    a convertor for converting a signal from said detector array, said convertor being connected to said detector array and to said microprocessor; and
    an output device connected to said microprocessor and adapted for receiving a tomographic model from said microprocessor.

14. The system according to claim 13, wherein said restricted beam device comprises a dual-energy level restricted beam device.

15. The system according to claim 13, wherein said controller is adapted to compare a pre-existing tomographic model with a current tomographic model.

16. The system according to claim 13, wherein:
said x-ray source travels along a single axis; and
said x-ray source simultaneously rotates around said single axis.

17. The system according to claim 13, wherein said X-ray source emits an X-ray beam comprising a cone configuration.

18. The system according to claim 17, wherein said restricted beam device comprises a dual-energy level restricted beam device.

19. The system according to claim 17, wherein said controller is adapted to compare a pre-existing tomographic model with a current tomographic model.

20. The system according to claim 17, wherein:
said x-ray source travels along a single axis; and
said x-ray source simultaneously rotates around said single axis.

21. A system for tomographically modeling a dental structure, which system comprises:
 a controller with a microprocessor and a memory device connected to the microprocessor, said controller being adapted for creating, storing, and comparing 3D digital tomographic models of a dental structure without the use of fiducial markers of said dental structure;
 an input device connected to the microprocessor;
 a positioning motor connected to the microprocessor and responsive to commands from said microprocessor;
 X-ray equipment including an X-ray source, a detector array, and a restricted beam device;
 a convertor for converting a signal from said detector array, said convertor being connected to said detector array and to said microprocessor; and
 an output device connected to said microprocessor and adapted for receiving a tomographic model from said microprocessor.

22. The system according to claim 21, wherein said restricted beam device comprises a dual-energy level restricted beam device.

23. The system according to claim 21, wherein said X-ray source emits an X-ray beam comprising a cone configuration.

24. The system according to claim 23, wherein said restricted beam device comprises a dual-energy level restricted beam device.

* * * * *